US010850127B2

(12) United States Patent
Overweg

(10) Patent No.: US 10,850,127 B2
(45) Date of Patent: Dec. 1, 2020

(54) CHARGED PARTICLE BEAM THERAPY AND MAGNETIC RESONANCE IMAGING

(71) Applicant: KONINKLIJKE PHILIPS N.V., Eindhoven (NL)

(72) Inventor: Johannes Adrianus Overweg, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 842 days.

(21) Appl. No.: 15/319,984

(22) PCT Filed: Jun. 19, 2015

(86) PCT No.: PCT/EP2015/063783
§ 371 (c)(1),
(2) Date: Dec. 19, 2016

(87) PCT Pub. No.: WO2015/197475
PCT Pub. Date: Dec. 30, 2015

(65) Prior Publication Data
US 2017/0120075 A1    May 4, 2017

(30) Foreign Application Priority Data
Jun. 27, 2014 (EP) ..................... 14174681

(51) Int. Cl.
*A61N 5/10* (2006.01)
*G01R 33/38* (2006.01)
(Continued)

(52) U.S. Cl.
CPC ............ *A61N 5/1049* (2013.01); *A61B 5/055* (2013.01); *A61N 5/1081* (2013.01);
(Continued)

(58) Field of Classification Search
CPC ................ A61N 5/1049; A61N 5/1081; A61N 2005/1087; A61N 2005/1055;
(Continued)

(56) References Cited

U.S. PATENT DOCUMENTS 6,198,957 B1    3/2001 Green
6,714,011 B1 *  3/2004 Aldefeld .............. G01R 33/482
                                                324/318
(Continued)

FOREIGN PATENT DOCUMENTS

WO    WO-2012164527 A1 * 12/2012 ......... G01R 33/4808
WO       20140121991 A1    8/2014

OTHER PUBLICATIONS

Lagendijk etal:"MRI/linac integration",Radiotherapy and Oncology, Elsevier,Ireland,vol. 86, No. 1, Nov. 26, 2007 (Nov. 26, 2007), pp. 25-29,XP022423061,ISSN:0167-8140, DOI:10.1016/J.RADONC. 2007.10.034.
St. Aubin et al "Magnetic Decoupling of the Linac in a Low Field Biplanar Linac-MR System" Med. Phys. 37 (9) Sep. 2010 p. 4755-4761.

*Primary Examiner* — Pascal M Bui Pho
*Assistant Examiner* — Sean D Mattson
(74) *Attorney, Agent, or Firm* — Sherry Austin

(57) ABSTRACT

The present invention provides a medical apparatus (100) comprising a magnetic resonance imaging system (110) for acquiring magnetic resonance data from an imaging volume (122) covering at least partially a subject of interest (120), wherein the magnetic resonance imaging system (110) comprises a main magnet (112) for generating a magnetic field within the imaging volume (122), a particle beam apparatus (150) having a particle beam line (152) for a particle beam (154) of charged particles, including a gantry (156) configured for rotating around a rotational axis (R), which is arranged in the longitudinal direction of the main magnet (112), wherein the gantry (156) comprises at least one
(Continued)

bending magnet (158) for directing the particle beam (154) to an irradiation volume (124) within the imaging volume (122), an active compensation coil (200), which is arranged to substantially surround at least the imaging volume (122), and a control unit (132) for controlling the active compensation coil (200) for canceling a stray field caused by the at least one bending magnet (158) within the imaging volume (122) at least in the longitudinal direction of the main magnet (112). The present invention also provides a shielding method for use in the above medical apparatus (100).

20 Claims, 8 Drawing Sheets

(51) Int. Cl.
  *G01R 33/48* (2006.01)
  *G01R 33/3875* (2006.01)
  *A61B 5/055* (2006.01)
(52) U.S. Cl.
  CPC ..... *G01R 33/3806* (2013.01); *G01R 33/3875* (2013.01); *G01R 33/4808* (2013.01); *A61N 2005/1055* (2013.01); *A61N 2005/1087* (2013.01)
(58) Field of Classification Search
  CPC ................ A61B 5/055; G01R 33/4808; G01R 33/3806; G01R 33/3875
  See application file for complete search history.

(56) References Cited

U.S. PATENT DOCUMENTS

| | | | |
|---|---|---|---|
| 6,862,469 B2 | 3/2005 | Bucholz et al. | |
| 7,960,710 B2 | 6/2011 | Kruip et al. | |
| 8,427,148 B2 | 4/2013 | O'Connor | |
| 8,554,302 B2 | 10/2013 | Gross et al. | |
| 8,838,202 B2 | 9/2014 | Kruip | |
| 8,981,779 B2 * | 3/2015 | Shvartsman | G01R 33/4812 324/320 |
| 9,664,763 B2 * | 5/2017 | Amthor | G01R 33/4808 |
| 2005/0197564 A1 * | 9/2005 | Dempsey | A61B 5/055 600/411 |
| 2006/0181381 A1 * | 8/2006 | Markiewicz | G01R 33/3875 335/216 |
| 2008/0208036 A1 * | 8/2008 | Amies | A61N 5/1049 600/411 |
| 2009/0234219 A1 * | 9/2009 | Kruip | A61N 5/1049 600/411 |
| 2011/0012593 A1 | 1/2011 | Shvartsman et al. | |
| 2011/0196226 A1 * | 8/2011 | Gross | A61B 5/055 600/411 |
| 2011/0237859 A1 * | 9/2011 | Kuhn | A61N 5/1031 600/1 |
| 2011/0260727 A1 * | 10/2011 | Punchard | G01R 33/3875 324/318 |
| 2014/0084926 A1 * | 3/2014 | Amthor | G01R 33/4808 324/309 |
| 2015/0217136 A1 | 8/2015 | Stanescu et al. | |

* cited by examiner (State of the Art)

CHARGED PARTICLE BEAM THERAPY AND MAGNETIC RESONANCE IMAGING

CROSS REFERENCE TO RELATED APPLICATIONS

This application is a U.S. national phase application of International Application No. PCT/EP2015/063783, filed on Jun. 19, 2015, which claims the benefit of EP Application Serial No. 14174681.8 filed on Jun. 27, 2014 and is incorporated herein by reference.

FIELD OF THE INVENTION

The invention relates to the area of guiding of charged particles to a target zone within a subject of interest, whereby the particles are guided using magnetic resonance imaging.

BACKGROUND OF THE INVENTION

In charged particle beam therapy, an energetic charged particle beam is directed at a target zone of a subject. The primary mechanism for interaction of a beam comprising charged particles with matter is through the Coulomb force. The cross section for Coulomb collisions increases as the relative velocity of two particles decreases. As a charged particle beam travels through a subject, it loses energy more and more rapidly. The effect of this is that the majority of the energy of the particle beam is deposited near the end of the beam path. Therefore, a large peak of energy is deposited at the end of the beam path which is called the Bragg peak.

Accordingly, charged particle beam therapy allows very precise delivery of high dose to a target zone, e.g. to a tumor target, while minimizing the total dose to a subject of interest. However, even small movements of the subject of interest, e.g. of anatomical structures in the path of the beam or a displacement of the target zone, can lead to significant deviations of the delivered dose from the original dose plan. Therefore, it is desirable to use real-time imaging to track the subject of interest and to adapt the beam to the motion of the subject of interest including the motion of organs of the subject of interest. The accuracy of charged particle beam therapy can be significantly improved by real-time guidance based on magnetic resonance (MR) imaging.

In the field of charged particle beam therapy, different kinds of charged particles can be used for treatment of the subject of interest, e.g. as a cancer treatment. Accordingly, a source of charged particles is required and a beam path to direct the charged particle beam into the subject of interest. One example of charged particle beam therapy is Proton Therapy (PT), where protons are directed into the subject of interest. An example of a combined MR-Proton therapy apparatus is described in EP 2 379 172 B1.

For charged particle beam therapy, real-time magnetic resonance imaging (MRI) during the delivery of the charged particle beam is challenging because of the strong magnetic fields associated with MRI and strong magnetic fields used for directing the particle beam to the target zone. Hence, superposition of and interaction between the magnetic fields may cause severe problems, in particular for MRI.

A static magnetic field is used by Magnetic Resonance Imaging (MRI) scanners to align the nuclear spins of atoms as part of the procedure for producing images within the body of the subject of interest. During an MRI scan, Radio Frequency (RF) pulses generated by a transmitter coil cause perturbations to the local magnetic field, and RF signals emitted by the nuclear spins are detected by a receiver coil. These RF signals are used to construct the MRI images. The transmitter and receiver coils can also be integrated into a single transceiver coil. It is understood that the use of the term transceiver coil also refers to systems where separate transmitter and receiver coils are used.

Accordingly, the subject of interest is located within a magnetic resonance imaging (MRI) system, and a proton source is provided together with a gantry, which directs the protons into the subject of interest. The gantry is rotatable around a z-axis of the MRI system, i.e. around the z-axis of a main magnet of the MRI system, to direct the radiation towards the subject of interest in a direction substantially perpendicular to the z-axis, which is achieved using at least one bending magnet, also referred to as dipole magnet, in the gantry.

This setup brings the at least one bending magnet of the proton therapy system in close proximity to the main magnet of the MRI system. The bending magnet generates a strong dipole field, which can have a field strength of e.g. ~1.5 T, in a large aperture and potentially creates a strong stray-field in the direction perpendicular to the bending plane. Since this stray field drops off rapidly with distance from the dipole magnet, it also has components in other directions, notably along the direction of the MRI magnet's main field, i.e. in the direction of the z-axis. This field will cause image distortion and other artifacts. A static compensation of the PT field at the MRI system, e.g. using shimming, is not feasible because of the rotation of the bending magnets about the z-axis of the MRI system. Furthermore, the strength of the field of the dipole magnet has to be modulated along with modulation of the energy of the charged particles. The energy of the charged particles is adapted to move the Bragg zone along the beam direction, e.g. charged particles with increased energy enter further into the subject of interest than charged particles with lower energy. Depending on the energy of the charged particles, also the strength of the external field of the bending magnet will thus also be variable.

In this context, a method is known from document WO 2012/164527 A1 A for correcting a magnetic field of an MRI radiotherapy apparatus comprising a magnetic resonance imaging system and a radiation therapy system. The MRI system includes a magnet for generating the magnetic field within an imaging zone. The magnet generates a magnetic field with a zero crossing outside of the imaging zone. The medical apparatus further comprises a gantry configured for rotating a ferromagnetic component about a rotational axis. The method comprises the step of installing a magnetic correcting element located on a radial path perpendicular to the rotational axis. The magnetic correcting element is positioned on the radial path such that change in the magnetic field within the imaging zone due to the ferromagnetic component is reduced. The method further comprises repeatedly: measuring the magnetic field within the imaging zone; determining the change in the magnetic field in the imaging zone; and adjusting the position of the magnetic correcting element along the radial path if the change in the magnetic field is above a predetermined threshold.

Furthermore, post-published WO 2014/121991 A1 refers to a medical apparatus comprising a magnetic resonance imaging system; magnetic compensation coils for compensating for magnetic inhomogeneities within the imaging zone; a gantry operable for rotating about the imaging zone; a position sensor for measuring the angular position and the angular velocity of the gantry; at least one magnetic field distorting component in the gantry, a memory storing machine executable instructions and field correction data. The instructions cause a processor to: receive the position and angular velocity data from the position sensor; determine coil control commands for controlling the magnetic compensation coils using the field correction data, the position data and the angular velocity data; control the magnetic compensation coils to compensate for magnetic inhomogeneities within the imaging zone using the coil control commands; and acquire the magnetic resonance data.

SUMMARY OF THE INVENTION

It is an object of the invention to enable reliable magnetic resonance imaging when performing magnetic resonance imaging. It is a further aspect of the invention to improve particle beam treatments for providing a particle beam of charged particles to a subject of interest by improved guidance using improved magnetic resonance imaging. It is a particular object of the present invention to provide a medical apparatus comprising a magnetic resonance imaging system for acquiring magnetic resonance data from an imaging volume of a subject of interest and a particle beam line for providing a particle beam of charged particles and a shielding method which enable reliable compensation of a magnetic field of bending magnets for directing the particle beam to an irradiation volume within the imaging volume during operation of the particle beam apparatus within the imaging volume.

This object is achieved by a medical apparatus comprising a magnetic resonance imaging system for acquiring magnetic resonance data from an imaging volume covering at least partially a subject of interest, wherein the magnetic resonance imaging system comprises a main magnet for generating a magnetic field within the imaging volume, a particle beam apparatus having a particle beam line for providing a particle beam of charged particles, including a gantry configured for rotating around a rotational axis, which is arranged in the longitudinal direction of the main magnet, wherein the gantry comprises at least one bending magnet for directing the particle beam to an irradiation volume within the imaging volume, an active compensation coil, which is arranged to substantially surround at least the imaging volume and which is provided in proximity to an outer surface of the main magnet, and a control unit for controlling the active compensation coil for canceling a stray field caused by the at least one bending magnet within the imaging volume at least in the longitudinal direction of the main magnet.

This object is also achieved by a shielding method for use in a medical apparatus, comprising the steps of providing a magnetic resonance imaging system for acquiring magnetic resonance data from an imaging volume covering at least partially a subject of interest, wherein the magnetic resonance imaging system comprises a main magnet for generating a magnetic field within the imaging volume, providing a particle beam apparatus having a particle beam line for a particle beam of charged particles, including a gantry configured for rotating around a rotational axis, which is arranged in the longitudinal direction of the main magnet, wherein the gantry comprises at least one bending magnet for directing the particle beam to an irradiation volume within the imaging volume, providing an active compensation coil, which is arranged to substantially surround at least the imaging volume and which is provided in proximity to an outer surface of the main magnet, and controlling the active compensation coil for canceling a stray field caused by the at least one bending magnet within the imaging volume at least in the longitudinal direction of the main magnet.

Accordingly, the active compensation coil actively cancels the z-component of the stray field of the at least one bending magnet across the field of view or imaging volume of the MR magnet. Hence, the stray field of the at least one bending magnet of the particle beam apparatus is actively compensated in such a way that its component along a main field direction of the MR magnet, i.e. a longitudinal direction or z-axis of the MR magnet, is either homogeneous or zero over the imaging volume of the MR system. This is preferably applied for all rotational positions of the gantry of the particle beam apparatus and for all strengths of the magnetic field of the at least one bending magnet. Thus the disturbing effect of the particle beam apparatus, in particular of the at least one bending magnet of the particle beam apparatus, on the quality of the MR imaging is reduced or eliminated. The bending magnet is also referred to as dipole magnet.

Shielding of the at least one bending magnet itself, i.e. shielding the magnetic field at the source is not easy due to the great strength of this magnetic field. Passively shielding with ferromagnetic material would be problematic, because this shielding material would also be exposed to the stray field of the MRI magnet and thereby create additional field inhomogeneity across the imaging volume. Moreover, the strength of the magnetic field of the at least one bending magnet and hence also its stray field is not constant in time, but varies with the energy of the charged particles. As most treatment procedures involve a modulation of the energy of the charged particles in order to move the Bragg peak in beam direction, a static compensation is not suitable to cancel the effect of the magnetic field of the at least one bending magnet. These disadvantages can be overcome by the proposed active shielding using the active compensation coil.

Active compensation of the magnetic field of the at least one bending magnet is most efficient when the active compensation coil is as close as possible to the volume where the compensating field is required. Consequently, it is preferred to provide the active compensation coil as far away as possible from the at least one bending magnet. Therefore, it is preferred that the active compensation coil has its windings distributed over a cylindrical surface located just outside the cylindrical outer surface of the magnet, or outside the cylindrical outer surface of a cryostat of the main magnet. Preferably, the magnet of the MRI does not have any protrusions, so that the active compensation coil can be located in close proximity to the main magnet and as far away from the at least one bending magnet as possible. In some state of the art magnets, such protrusions are provided e.g. for cryogenic or vacuum ports, magnet support attachments, magnet feet, or other components.

Preferably, the gantry is provided to direct the beam of charged particles to the subject of interest with an angle perpendicular to the z-axis of the main magnet. Accordingly, the passage of the charged particles through the subject of interest can be limited to a minimum, thereby reducing a dose for the subject of interest.

The magnetic field of at least one of the bending magnets, i.e. the bending magnet closest to an outlet section of the gantry, is directed perpendicular to the z-axis of the magnet and rapidly drops off with distance from an outlet section of the gantry. Due to this field gradient, the field of the at least one bending magnet at the imaging volume of the MR magnet also has a z-component, which is zero in the z=0 plane and increases in magnitude away from this midplane of the MR magnet. For a tentative design of such a dipole magnet, the field gradient across the imaging volume is of the order of 100 ppm. For the proper operation of the MRI system it is most important and generally sufficient to eliminate this z-component of the field of the at least one bending magnet.

Preferably, the active compensation coil is provided with a suitable shape and current distribution, so that is generates essentially the same magnetic field pattern as the at least one bending magnet, but with opposite polarity. This is achieved by a respective design of the active compensation coil.

Preferably, the active compensation coil has a winding distribution, so that with a control of the current of the active compensating coil the resulting magnetic field, i.e. the magnetic field of the at least one bending magnet together with the magnetic field of the active compensation coil, has a uniform z-component over the entire field of view of the MR magnet, i.e. the imaging volume. The transverse components of the total field of the at least one bending magnet and the active compensation coil need not be zero. As long as the total transverse field is small enough that the vector sum of the transverse field and the main MRI magnet field is not significantly different from the magnetic field of the MR magnet, the imaging process of the MRI system will not be affected by the transverse field.

A preferred choice for the strength of the resulting z-component of the magnetic field of the at least one bending magnet of the particle beam apparatus and the active compensation coil is zero. Even with this design restriction, a high number of solutions for the current distribution in the active compensating coil can be obtained, i.e. the design of the active compensation coils is essentially not limited by this specification. The special case that also the transverse components of the net field of the at least one bending magnet and the compensation coil be zero is attractive because it would eliminate other possible interactions between the magnetic resonance imaging system and the particle beam apparatus. Nevertheless, this implementation requires a powerful design of the active compensation coil, which would result in a complex design compared to an active compensation coil for cancelling essentially the overall z-component of the magnetic field.

Preferably, a current pattern for the active compensation coil is be designed by first calculating or measuring a field map of the at least one bending magnet at the location of the imaging volume of the MR magnet. These field values can then be used as field targets for a coil optimization program using the stream function method. This is similar to what is normally used to design MR gradient coils. The cost function in the optimization can then be the total dissipation in the active compensation coil. The resulting current pattern is preferably discretized into windings each carrying the same operating current.

Further preferred, the active compensation coil also compensates the fields of other sources of magnetic fields of the particle beam apparatus. Preferably, the active compensation coil also compensates the fields of other sources of magnetic fields, which scale with the operating current in the at least one bending magnet.

Preferably, the a particle beam apparatus is a Proton Therapy (PT) apparatus for directing a beam of protons to the subject of interest. PT apparatus are known in the Art and do not have to be discussed in detail.

According to a preferred embodiment the active compensation coil is fixed to the gantry and rotatable together with the gantry around the rotational axis. With the active compensation coil fixed to the gantry, the active compensation coil can easily rotate with the gantry and the at least one bending magnet, so that magnetic fields generated by the at least one bending magnet and magnetic files for compensation thereof, which are generated by the active compensation coil, rotate together. This facilitates compensation of the rotating magnetic fields.

According to an alternative embodiment, the active compensation coil is rotatable around the rotational axis of the gantry, but the rotation of the active compensation coil is controlled independently from the rotation of the gantry. Accordingly, the active compensation coil can be easily added to existing medical apparatus. It can also be added easily existing particle beam apparatus. The design of the existing apparatus does not have to be changed.

According to a preferred embodiment the active compensation coil is fixed to an outlet section of the gantry. The outlet section of the gantry refers to the part of the gantry, where the particle beam leaves the gantry to enter the subject of interest. Active compensation of the magnetic field of the at least one bending magnet is most efficient when the active compensation coil is as close as possible to the volume where the compensating field is required. Consequently, it is preferred to provide the active compensation coil as far away as possible from the at least one bending magnet, i.e. the active compensation coil is fixed to the outlet section, which is close to the main magnet.

According to a preferred embodiment the active compensation coil comprises a cylindrical support structure and a set of windings arranged at the support structure for carrying a compensation current. The support structure and the windings are preferably made of non-ferrous materials to avoid influences on the magnetic field inside the main magnet, in particular in the imaging volume. Preferably, the windings are made of copper. The windings of the active compensation coil can be placed on an outer or inner surface of the support structure. The windings are preferably provided on the support structure in accordance with a designed current distribution pattern of the active compensation coil as discussed above.

According to a preferred embodiment the active compensation coil comprises a metal sheet, whereby electric paths are cut into the metal sheet, and the metal sheet is bent around a cylindrical support structure. The support structure and the metal sheet are preferably made of non-ferrous materials to avoid influences on the magnetic field inside the main magnet, in particular in the imaging volume. Preferably, the metal sheet is made of copper. The metal sheet of the active compensation coil can be placed on an outer or inner surface of the support structure. The electric paths are preferably provided in the metal sheet in accordance with a designed current distribution pattern of the active compensation coil as discussed above.

According to a preferred embodiment the active compensation coil is provided with at least one opening for passage of the particle beam. The at least one opening refers to an area of the active compensation coil without conductive elements. Hence, the at least one opening serves as a window for the beam of charged particles to reach the subject of interest. Multiple openings can be provided e.g. in the case of a non-rotating active coil, so that the beam of charged particles can be directed to the subject of interest from multiple directions through the multiple openings.

Preferably, the active compensation coil has mirror symmetry with respect to a plane including the z-axis of the main magnet. Further preferred, no conductors of the active compensation coil cross this symmetry plane. Accordingly, a mechanical split in the cylindrical structure of the active compensation coil and its support structure can be provided to allow the active compensation coil to be installed around the MRI magnet in two halves, which are joined together by bolts or other means after placing the coil around the MRI main magnet. The windings of the two halves of the active compensation coil are preferably connected in series.

According to a preferred embodiment the active compensation coil is cooled by air, through forced or natural convection, or by water flowing through cooling channels mounted on the surface of the active compensation coil or through the windings of the active compensation coil itself if these are made from a hollow conductor. Since the active compensation coil preferably rotates with the bending dipole, it is possible to use a water-cooling system of the dipole magnet to also cool the active compensation coil.

According to a preferred embodiment the control unit is adapted to control the active compensation coil to be energized with a current proportional to a current in the at least one bending magnet. Hence, the compensation of the magnetic fields of the at least one bending magnet can be facilitated, since variation in the field strength of the at least one bending magnet, which impact on the strength of the stray field, are directly applied to the active compensation coil as well. With a proper design of the active compensation coil as discussed above, compensation of the stray fields can be automatically performed by driving the active compensation coil with the proportional current.

According to a preferred embodiment the at least one bending magnet and the active compensation coil are provided having the same operating current for matching fields, and the active compensation coil and the at least one bending magnet are electrically connected in series to be driven by the same operating current. Hence, the compensation of the magnetic fields of the at least one bending magnet can be further facilitated, since variations in the field strength of the at least one bending magnet, which impact on the strength of the stray field, are directly compensated by the active compensation coil. With a proper design of the active compensation coil as discussed above, compensation of the stray fields can be automatically performed.

According to a preferred embodiment the medical apparatus comprises a driving device for powering the active compensation coil, and the control unit is adapted to control the driving device using magnet set-point information from the particle beam apparatus. Hence, the active compensation coil can be driven independently from the current through the at least one bending magnet, i.e. the active compensation coil is driven in an independent mode. In this independent mode of operation it is useful to generate and use a look-up table of proper values of compensation currents in dependence of a current in the bending magnet. The look-up table can be generated by magnetic simulation or by measurement of the fields of dipole magnet and the active compensation coil. If magnetic hysteresis in ferromagnetic parts of the dipole magnet affects the external field in dependence of current, it is advantageous to provide separate look-up tables for the cases that the dipole current is increased or decreased.

According to a preferred embodiment the active compensation coil comprises a multilayer coils setup with at least two coaxial coil layers. The multilayer setup can be achieved e.g. by providing a cylindrical support structure, where a set of windings is provided on its inner cylindrical surface and another set of windings is provided on its outer cylindrical surface, thereby forming two coil layers in this embodiment. Preferably, the coil layers can be driven independently. Additional coil layers can be added to an active compensation coil to compensate for magnetic fields generated by any additional source of magnetic fields, e.g. when multiple bending and/or scanning magnets are used. The multilayer coil setup enables compensation of non-linearities in the external field of the dipole magnet, which might be caused by saturation in the iron return yoke of the bending magnet. Furthermore, in case the particle beam apparatus comprises multiple magnets, which are driven with currents with different time dependency, the multilayer setup is preferably used to compensate for the magnetic fields generated by these sources of magnetic stray fields.

Alternatively, the active compensation coil may be provided as an active compensation coil assembly comprising at least two independent coils. The principles discussed above in respect to the multilayer coil setup also apply to the active compensation coil assembly comprising at least two independent coils.

According to a preferred embodiment the active compensation coil comprises at least one correction winding. Typically, the at least one correction winding is small compared to the size of the active compensation coil. The at least one correction winding enables a fine-adjustment of the compensating effect which might be desired to compensate field errors due to manufacturing or alignment accuracy.

According to a preferred embodiment the method comprises aligning the active compensation coil to the at least one bending magnet. In particular, when the active compensation coil is attached to the gantry, which rotates around the centerline of the MR magnet, the compensation coil needs to be accurately aligned to the at least one bending magnet. With the alignment of the at least one bending magnet and the active compensation coil, the field patterns of the at least one bending magnet and the active compensation coil can match each other, which facilitates the compensation of the magnetic field of the at least one bending magnet.

The principles discussed above in respect to the medical apparatus apply also, when the active compensation coil is used together with the particle beam apparatus alone, i.e. without the MRI system. Hence, a cylindrical space can be provided inside the active compensation coil, where magnetic stray fields can be reliably compensated, at least in the direction of the rotational axis of the gantry.

BRIEF DESCRIPTION OF THE DRAWINGS

These and other aspects of the invention will be apparent from and elucidated with reference to the embodiments described hereinafter. Such an embodiment does not necessarily represent the full scope of the invention, however, and reference is made therefore to the claims and herein for interpreting the scope of the invention.

In the drawings.

DETAILED DESCRIPTION OF EMBODIMENTS

Figure 1:
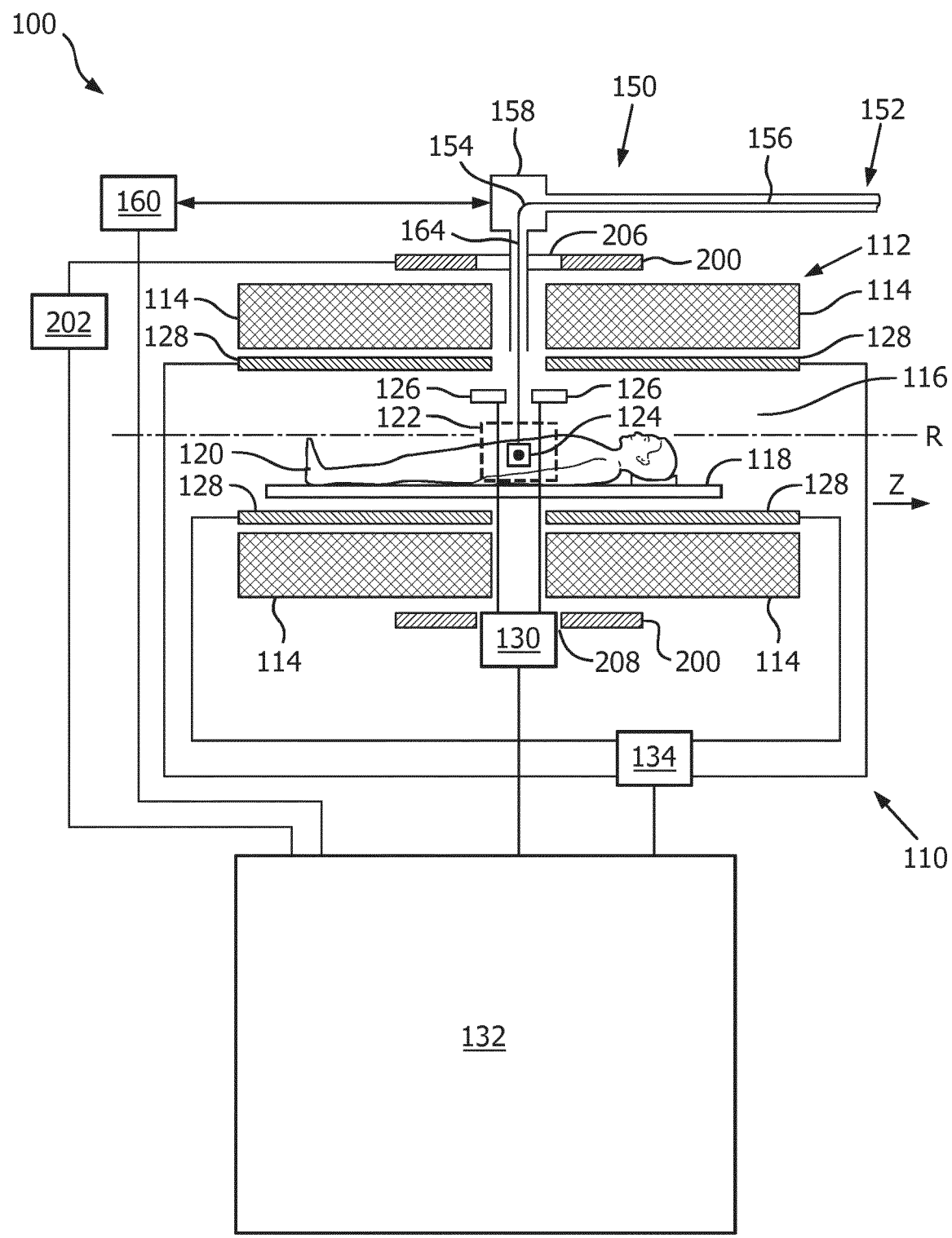
FIG. 1 shows a generalized cross-sectional view of an embodiment of a medical apparatus according to a first embodiment with an active compensation coil.
Figure 2:
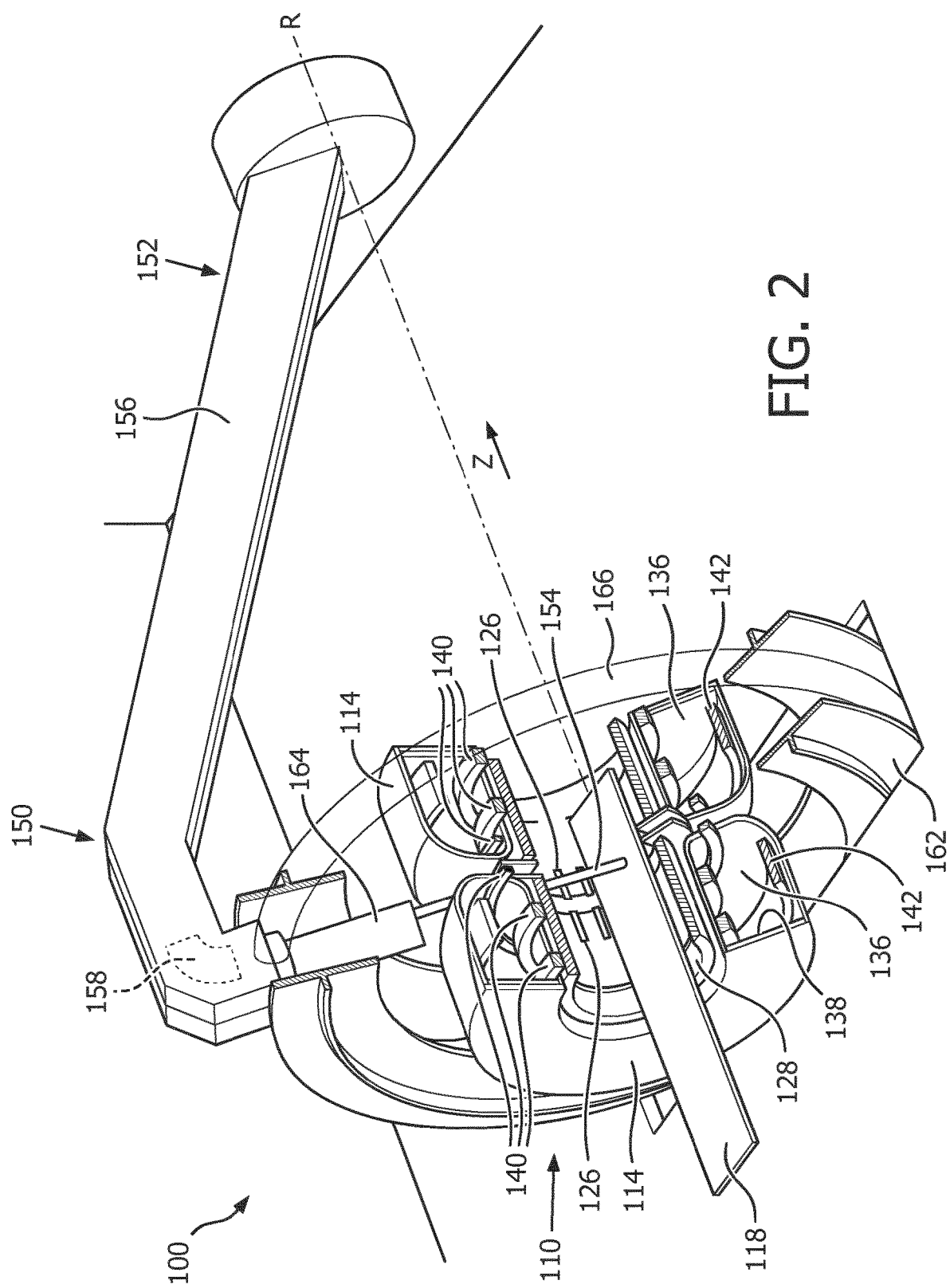
FIG. 2 shows the medical apparatus according to the first embodiment of FIG. 1 in a perspective view, whereby the active compensation coil is omitted.

FIGS. 1 and 2 show a medical apparatus 100 according to a preferred embodiment.

The medical apparatus 100 comprises a magnetic resonance imaging (MRI) system 110 that comprises a magnetic resonance (MR) magnet 112, also referred to as main magnet, which is provided as split magnet with two sub-magnets 114. As can be seen in detail in FIG. 2, each sub-magnet 114 comprises a cryogenic chamber 136, which is provided with a radiation shield 138. Within the cryogenic chamber 136 are arranged inner superconducting coils 140 adapted for generating the main magnetic field and an outer superconducting shielding coil 142. The superconducting shielding coil 142 is adapted such that there is a region of zero magnetic field surrounding the sub-magnet 114.

Within a bore 116 of the sub-magnets 114, there is provided a support 118 adapted for receiving a subject of interest 120. Between the two sub-magnets 114, there is an imaging volume 122 where the magnetic field is uniform enough that magnetic resonance imaging data can be acquired. Within the imaging volume 122 there is a irradiation zone 124, also referred to as target zone 124, which is discussed later in detail. Magnetic resonance imaging data is acquired using a split transceiver coil 126 in this embodiment. Spatial encoding of the information is performed by means of a split gradient coil 128. In this embodiment, the gradient coil 128 is located within the bore 116 of the main magnet 112.

In this embodiment, the split transceiver coil 126 is set directly on the subject of interest 120. In other embodiments the coils used for acquiring magnetic resonance imaging data can be mounted within the bore 116 of the MR magnet 112, they can be mounted on supports, or they can be mounted to the gradient coil 128.

The transceiver coil 126 is connected to a transceiver 130. The transceiver 130 is able to emit and also receive radio frequency signals. The transceiver 130 interfaces with a control unit 132. The control unit 132 is a control circuit for controlling the active compensation coil 200 for canceling a stray field caused by the bending magnet 158 within the imaging volume 122 at least in the longitudinal direction of the main magnet 112. The split gradient coil 128 is powered by a gradient amplifier 134, which is controlled by the control unit 132. The gradient amplifier 134 is a power amplifier capable of supplying the gradient coils 128 with current. The control unit 132 is a data processing device which is adapted for constructing images from magnetic resonance data obtained by the transceiver 126.

Figure 3:
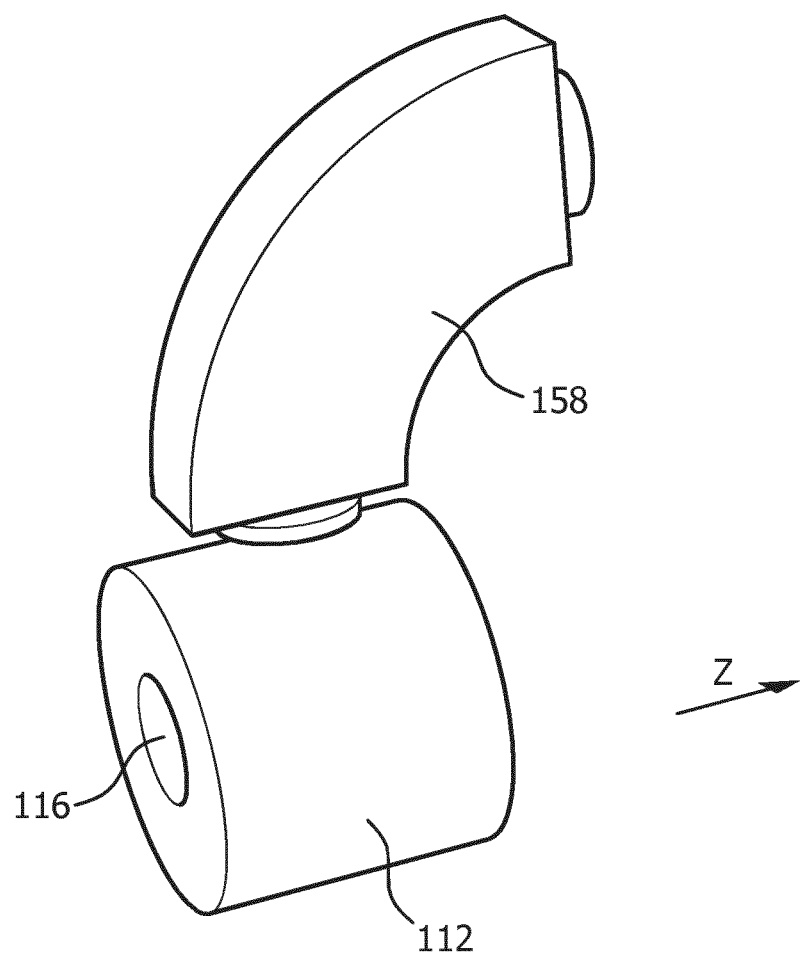
FIG. 3 shows a schematic arrangement of a bending magnet and a MR magnet in accordance with FIG. 2 in a perspective view.

The medical apparatus 100 further comprises a particle beam apparatus 150, which is a Proton Therapy (PT) apparatus in this embodiment. The PT apparatus 150 has a particle beam line 152 for a particle beam 154 of charged particles, including a gantry 156 configured for rotating around a rotational axis R, which is arranged in the longitudinal direction of the main magnet 112. The gantry comprises one bending magnet 158 for directing the particle beam 154 to the irradiation volume 124 within the imaging volume 122. In this embodiment, the particle beam 154 is directed to the subject of interest 120 with an angle perpendicular to the z-axis of the main magnet 112. Additional bending magnets, which are provided in the gantry 156, are not visible and are also not discussed in detail. FIG. 3 schematically depicts an arrangement of a bending magnet 158 and a MR magnet 112. The MR magnet 112 is depicted as a single magnet. Nevertheless, the particular design of the MR magnet 112 is as described above.

The PT apparatus 150 comprises guiding means 160, which are provided for controlling the bending magnet 158. The control unit 132 is adapted for controlling the guiding means 160. The guiding means 160 are adapted for directing the particle beam 154 to the irradiation volume 124. As can be seen in FIGS. 1 and 2, because of the split design of the main magnet 112, the transceiver coil 126 and the gradient coil 128, the particle beam 154 does not intersect the main magnet 112, the transceiver coil 126 and the gradient coil 128.

The PT apparatus 150 further comprises a rotatable support 162 for supporting the gantry 156. As can be seen in FIG. 2, the rotatable support 162 surrounds the MRI system 110. The rotatable support 162 supports the gantry 156 in an area of an outlet section 164, where the particle beam 154 exits the gantry 156.

Pulsed electromagnets used to scan the particle beam 154 are preferably located inside a low-field ring 166; this allows the use of efficient scanning magnets with a ferromagnetic return yoke.

Figure 4:
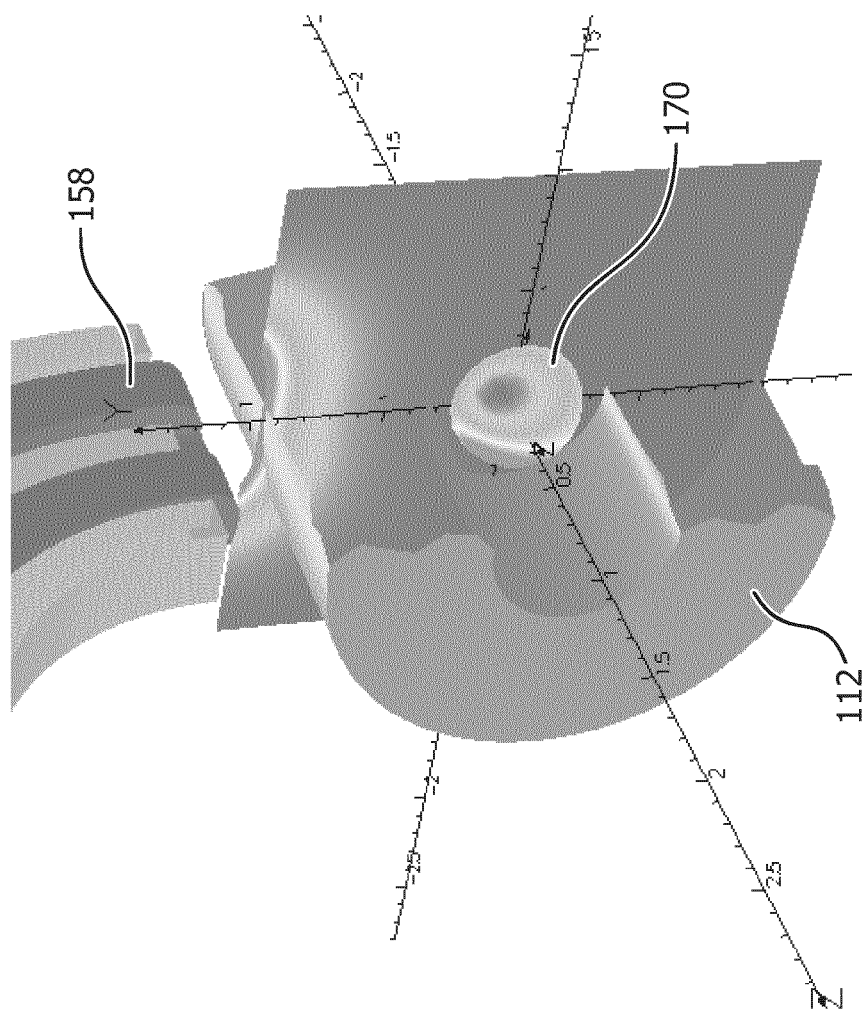
FIG. 4 shows a magnetic field distribution in the MR magnet of a MR system of the medical apparatus of FIG. 1 without active shielding as known from the prior Art in a perspective, cross-sectional view.
Figure 4:

As can be seen in FIG. 4, when operating the MRI system 110 and the PT apparatus 150 together, the bending magnet 158 causes inhomogeneities in the magnet field within the main magnet 112, as can be seen by the field distribution sphere 170.

The PT apparatus 150 further comprises an active compensation coil 200 to provide a homogeneous magnetic field within the MR magnet 112. The active compensation coil 200 is arranged to substantially surround at least the imaging volume 122. The active compensation coil 200 is further provided in proximity to an outer surface of the main magnet 112. In this position, the active compensation coil 200 is fixed to the outlet section 164 of the gantry 156 and rotatable together with the gantry 156 around the rotational axis R.

The active compensation coil 200 is driven via driving unit 202. The driving unit 202 is a driving device and a driving circuit for powering the active compensation coil 200. The control unit 132 controls the active compensation coil 200 via the driving unit 202. Furthermore, the control unit 132 controls the active compensation coil 200 for canceling a stray field caused by the bending magnet 158 within the imaging volume 122 in the longitudinal direction of the main magnet 112. In this embodiment, the control unit 132 controls the active compensation coil 200 to be energized using the driving unit 202 with a current proportional to a current in the bending magnet 158.

Hence, the control unit 132 controls the active compensation coil 200 to actively cancel the z-component of the stray field of the bending magnet 158 across the imaging volume 122 of the MR magnet 112, so that its component along the longitudinal direction of the MR magnet 112 is either homogeneous or zero within the imaging volume 122. This control is applied for all rotational positions of the gantry 158 of the particle beam apparatus 150 and for all strengths of the magnetic field of the bending magnet 158.

In this embodiment the active compensation coil 200 is designed with a suitable shape and current distribution, so that is generates essentially the same magnetic field pattern as the bending magnet 158, but with opposite polarity. Furthermore, the active compensation coil 200 is aligned to the bending magnet 158, so that field patterns of the bending magnet 158 and the active compensation coil 200 match each other. Still further, the active compensation coil 200 has a winding distribution, so that with a control of the current of the active compensation coil 200 the resulting magnetic field, i.e. the magnetic field of the at least one bending magnet together with the magnetic field of the active compensation coil, has a uniform z-component over the entire imaging volume of the MR magnet 112.

Figure 5:
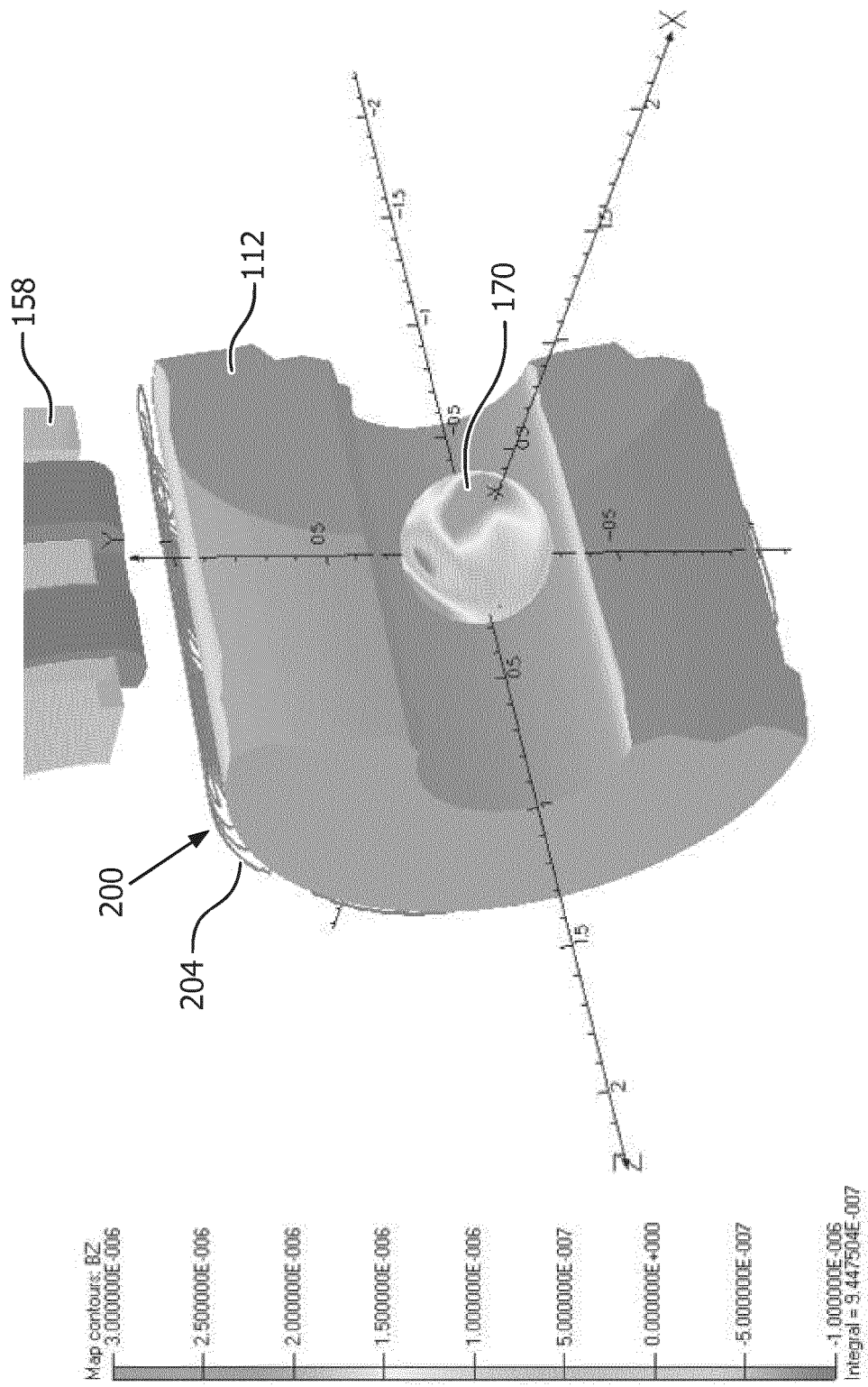
FIG. 5 shows a magnetic field distribution in the MR magnet of a MR system of the medical apparatus of FIG. 1 with an active compensation coil in a perspective, cross-sectional view.
Figure 6:
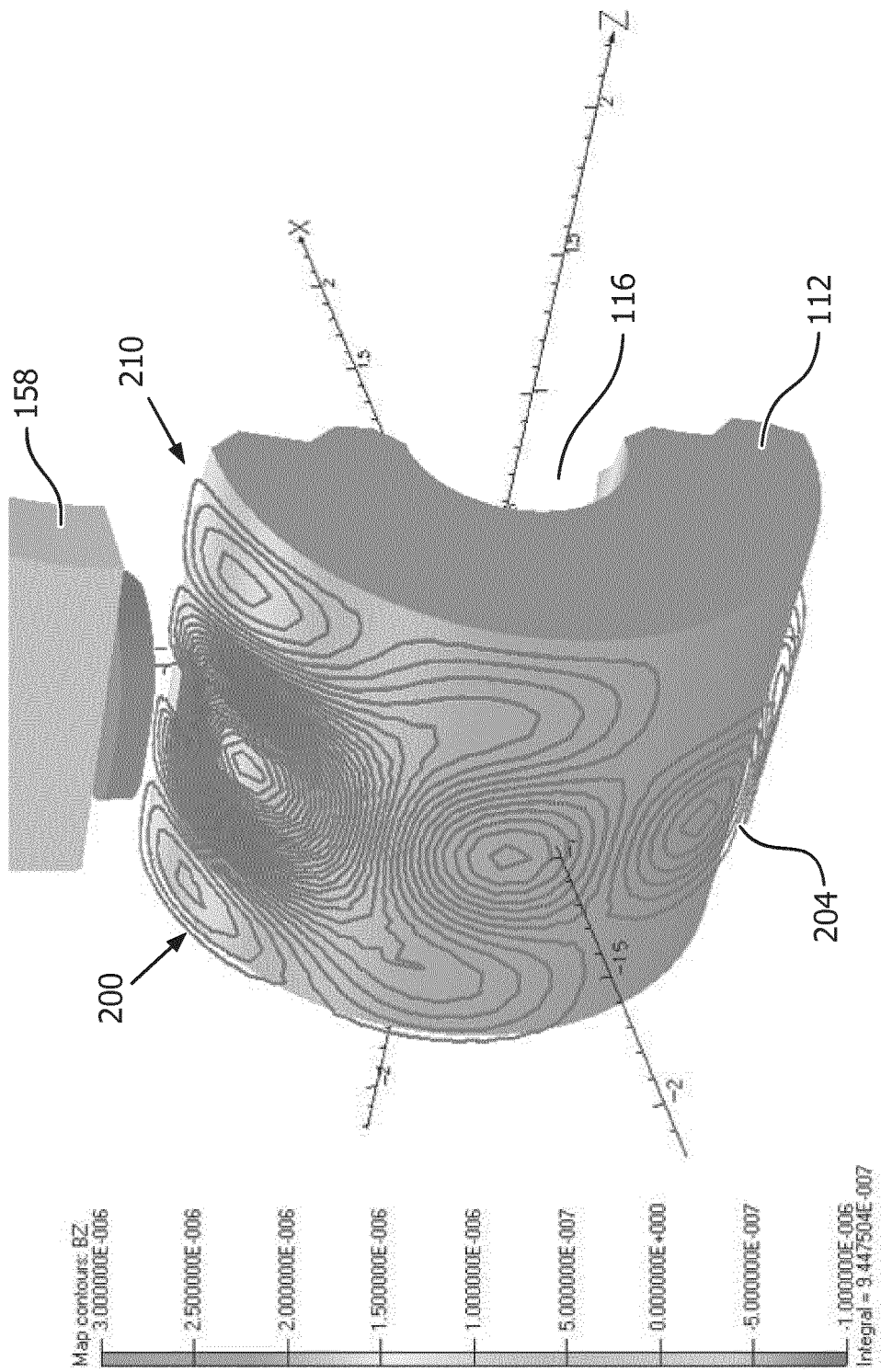
FIG. 6 shows windings of one half of an active compensation coil in a perspective, cross-sectional view together with the MR magnet of the MR system of the medical apparatus in accordance with FIG. 5, with the cut-plane of the drawing located at a symmetry plane of the compensation coil.
Figure 7:
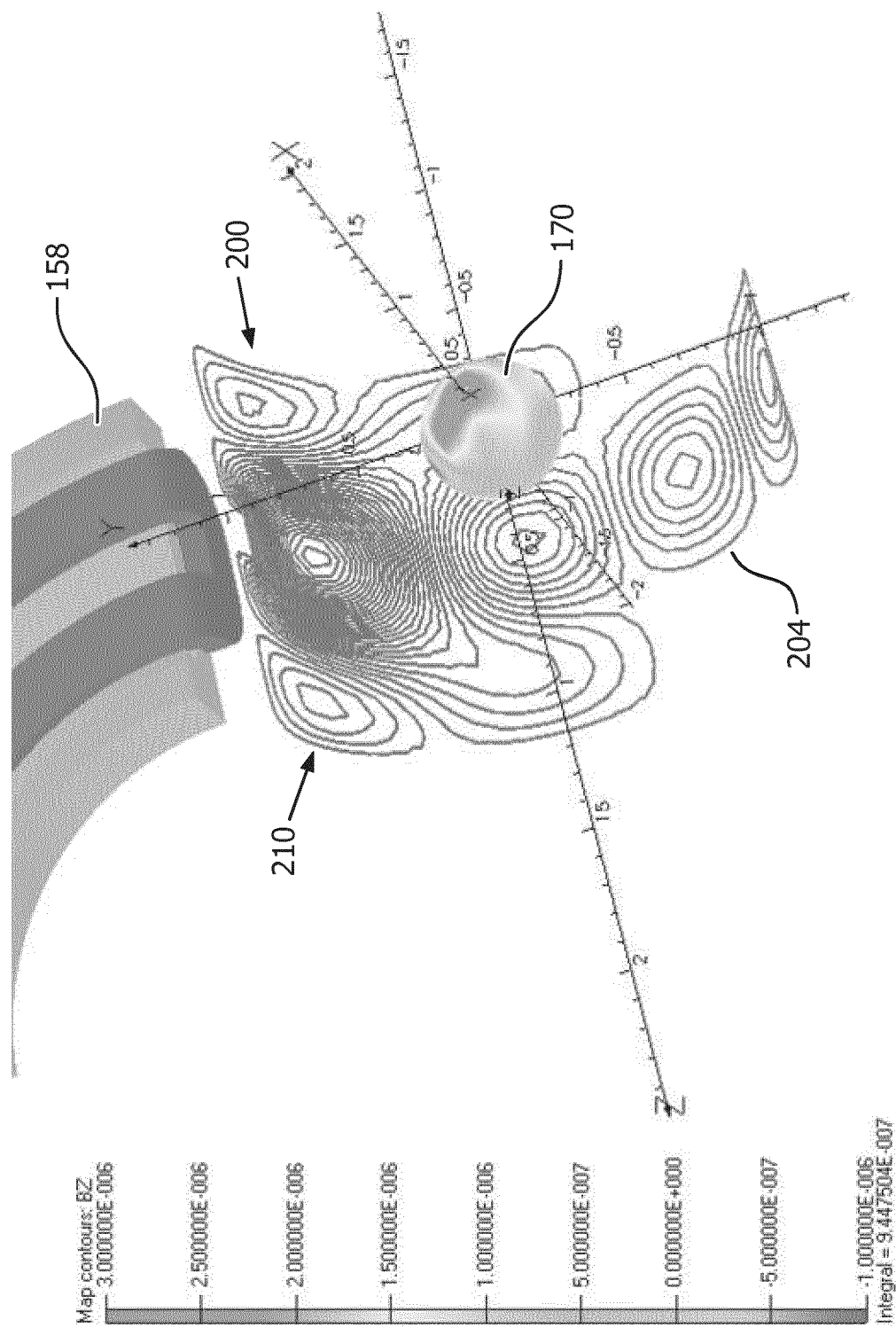
FIG. 7 shows the windings of one half of the active compensation coil as shown in FIGS. 5 and 6 in a perspective, cross-sectional view without the MR magnet, with the cut-plane of the drawing located at the symmetry plane of the compensation coil.

The active compensation coil 200 comprises a cylindrical support structure, which is not shown in the Figures, and a set of windings 204 arranged at the support structure for carrying a compensation current, as can be seen in FIGS. 5-7. The support structure and the windings 204 are made of non-ferrous materials. The windings 204 are formed of copper wire. In this embodiment, the windings 204 of the active compensation coil 200 are placed on an outer surface of the support structure. In an alternative embodiment, the windings 204 of the active compensation coil 200 are placed on an inner surface of the support structure. The windings 204 are provided on the support structure in accordance with a designed current distribution pattern of the active compensation coil 200 as described below.

In an alternative embodiment, the active compensation coil 200 comprises a metal sheet, whereby electric paths are cut into the metal sheet, and the metal sheet is bent around a cylindrical support structure. The support structure and the metal sheet are made of non-ferrous materials. The metal sheet is made of copper. The metal sheet of the active compensation coil 200 is either placed on an outer or inner surface of the support structure.

Figure 8:
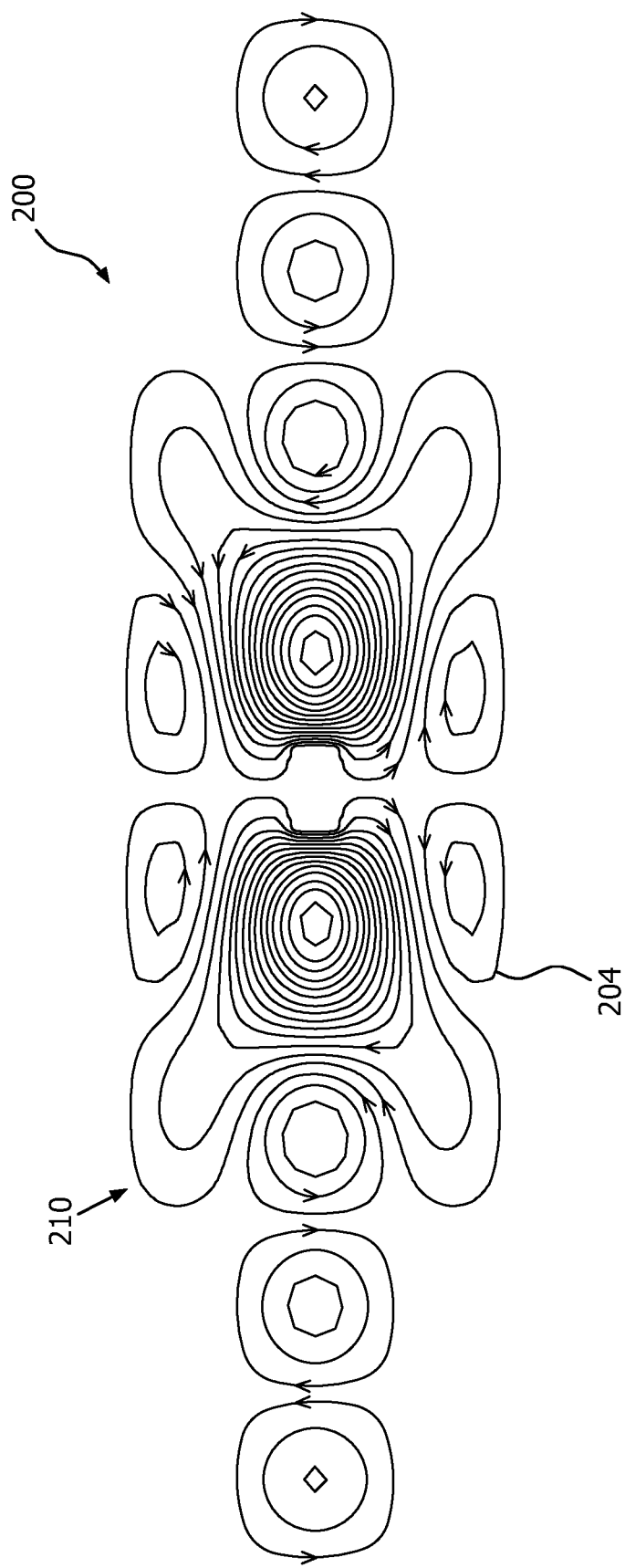
FIG. 8 shows a planar view the windings of one half of the active compensation coil of an active compensation coil in accordance with FIG. 7, where half of the windings has been omitted for clarity reasons.

As can be best seen in FIGS. 7 and 8, the active compensation coil 200 comprises two symmetric half coils 210, one of which is shown in FIGS. 7 and 8. In FIG. 8, only half of the windings 204 of the active compensation coil 200 are depicted compared to FIG. 7 for clarity reasons. Nevertheless, in an alternative embodiment, the active compensation coil 200 is provided with half of the windings 204 compared to the embodiment shown in FIG. 7. In this case, the active compensation coil 200 can be driven with the double current compared to the active compensation coil 200 shown in FIG. 7 in order to achieve the same active compensation.

With the two half coils 210, the active compensation coil 200 is provided with mirror symmetry with respect to a plane including the z-axis of the main magnet 112. Each half coil 210 is provided with its windings 204 being separated from the windings 204 of the respective other half coil 210, so that no windings 204 of the active compensation coil 200 cross this symmetry plane. The windings 204 of the two half coils 210 are connected in series, even though they appear to be provided in individual windings 204 in the figures. Hence, the same current is applied to the windings 204 shown e.g. in FIG. 8. A direction of the current is indicated in FIG. 8 by the arrows added to the windings 204.

In this embodiment the active compensation coil 200 is cooled by air, either through forced or natural convection. In an alternative embodiment, the windings are provided as hollow conductors for circulation of water as coolant. In a still further embodiment, cooling channels are mounted on the surface of the active compensation coil 200 to enable water circulation for cooling.

As can be seen in FIG. 1, the active compensation coil 200 is provided with an opening 206 for passage of the particle beam 154. The opening 206 refers to an area of the active compensation coil 200 without conductive elements, i.e. without windings 204. As can be seen in FIG. 1, a connection window 208 is provided for connection of the split transceiver coil 126 and the transceiver 130.

A current pattern for the windings 204 of the active compensation coil 200 is be designed by first calculating or measuring a field map of the at least one bending magnet 158 at the location of the imaging volume 122 of the MR magnet 112. These field values are used as field targets for a coil optimization program using a stream function method similar to what is normally used to design MR gradient coils. The cost function in the optimization is the total dissipation in the active compensation coil 200. The resulting current pattern is preferably discretized into the windings 204 each carrying the same operating current. The active compensation coil 200 in an alternative embodiment also compensates the fields of other sources of magnetic fields of the particle beam apparatus 150, in particular the active compensation coil 200 compensates the fields of other sources of magnetic fields, which scale with the operating current in the bending magnet 158. The active compensation coil 200 also comprises correction windings.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

REFERENCE SYMBOL LIST 100 medical apparatus
110 magnetic resonance imaging (MRI) system
112 magnetic resonance (MR) magnet, main magnet
114 submagnet
116 bore
118 support
120 subject of interest
122 imaging volume
124 irradiation volume, target zone
126 split transceiver coil
128 split gradient coil
130 transceiver
132 control unit
134 gradient amplifier
136 cryogenic chamber 138 radiation shield
140 inner superconducting coil
142 outer superconducting coil
150 particle beam apparatus, proton therapy apparatus
152 particle beam line
154 particle beam
156 gantry
158 bending magnet
160 guiding means
162 rotatable support
164 outlet section
166 low-field ring
170 field distribution sphere
200 active compensation coil
202 driving unit
204 winding
206 opening
208 connection window
210 half coil

The invention claimed is:

1. A medical apparatus, comprising
a magnetic resonance imaging system for acquiring magnetic resonance data from an imaging volume covering at least partially a subject of interest, wherein the magnetic resonance imaging system comprises a main magnet for generating a magnetic field within the imaging volume,
a particle beam apparatus having a particle beam line for a particle beam of charged particles, including a gantry configured for rotating around a rotational axis, which is arranged in the longitudinal direction of the main magnet, wherein the gantry comprises at least one bending magnet for directing the particle beam to an irradiation volume within the imaging volume,
an active compensation coil, which is arranged to substantially surround at least the imaging volume and which is provided in proximity to an outer surface of the main magnet, and
a control circuit for controlling the active compensation coil for canceling a stray field caused by the at least one bending magnet within the imaging volume at least in the longitudinal direction of the main magnet.

2. The medical apparatus according to claim 1, wherein the active compensation coil is fixed to the gantry and rotates together with the gantry around the rotational axis.

3. The medical apparatus according to claim 2, wherein the active compensation coil is fixed to an outlet section of the gantry where the particle beam exits the gantry to enter the subject of interest.

4. The medical apparatus according to claim 2, wherein current applied to the active compensation coil is varied in proportion with a current proportional to a current in the at least one bending magnet.

5. The medical apparatus according to claim 1, whereby the active compensation coil comprises a cylindrical support structure and a set of windings arranged at the support structure for carrying a compensation current.

6. The medical apparatus according to claim 1, wherein the active compensation coil comprises a metal sheet, whereby electric paths are cut into the metal sheet, and the metal sheet is bent around a cylindrical support structure.

7. The medical apparatus according to claim 1, wherein the active compensation coil is provided with at least one opening for passage of the particle beam.

8. The medical apparatus according to claim 1, wherein the control circuit is adapted to control the active compensation coil to be energized with a current proportional to a current in the at least one bending magnet.

9. The medical apparatus according to claim 1, wherein the at least one bending magnet and the active compensation coil are provided having the same operating current for matching fields, and the active compensation coil and the at least one bending magnet are electrically connected in series to be driven by the same operating current.

10. The medical apparatus according to claim 1, wherein the medical apparatus comprises a driving circuit for powering the active compensation coil, and the control circuit is adapted to control the driving circuit using magnet set-point information from the particle beam apparatus.

11. The medical apparatus according to claim 1, wherein the active compensation coil comprises a multilayer coils setup with at least two coaxial coil layers.

12. The medical apparatus according to claim 1, wherein the active compensation coil comprises at least one correction winding.

13. The medical apparatus according to claim 1, wherein the active compensation coil generates a magnetic field pattern with a polarity opposite to a magnetic field pattern of the at least one bending magnet.

14. The medical apparatus according to claim 1, wherein the active compensation coil rotates with the at least one bending magnet.

15. The medical apparatus according to claim 1, wherein current applied to the active compensation coil is varied in proportion with variation in field strength of the at least one bending magnet.

16. The medical apparatus according to claim 1, wherein a current applied to the active compensation coil is varied by the control circuit based on a field strength of the at least one bending magnet.

17. A shielding method for use in a medical apparatus, comprising:
providing a magnetic resonance imaging system for acquiring magnetic resonance data from an imaging volume covering at least partially a subject of interest, wherein the magnetic resonance imaging system comprises a main magnet for generating a magnetic field within the imaging volume,
providing a particle beam apparatus having a particle beam line for a particle beam of charged particles, including a gantry configured for rotating around a rotational axis, which is arranged in the longitudinal direction of the main magnet, wherein the gantry comprises at least one bending magnet for directing the particle beam to an irradiation volume within the imaging volume,
providing an active compensation coil, which is arranged to substantially surround at least the imaging volume and which is provided in proximity to an outer surface of the main magnet, and
controlling the active compensation coil for canceling a stray field caused by the at least one bending magnet within the imaging volume at least in the longitudinal direction of the main magnet.

18. The shielding method according to claim 17, further comprising aligning the active compensation coil to the at least one bending magnet.

19. A medical apparatus, comprising
a magnetic resonance imaging system configured to acquire magnetic resonance data from an imaging volume covering at least partially a subject of interest, wherein the magnetic resonance imaging system comprises a main magnet that generates a magnetic field within the imaging volume;

a particle beam apparatus having a particle beam line for a particle beam of charged particles, including a gantry configured for rotating around a rotational axis, which is arranged in the longitudinal direction of the main magnet, wherein the gantry comprises at least one bending magnet that directs the particle beam to an irradiation volume within the imaging volume; and an active compensation coil, which is arranged to substantially surround at least the imaging volume, which is provided in proximity to an outer surface of the main magnet, and which is driven to cancel a stray field caused by the at least one bending magnet within the imaging volume at least in the longitudinal direction of the main magnet.

20. The medical apparatus according to claim 19, wherein the active compensation coil is fixed to the gantry and rotates together with the gantry around the rotational axis.

* * * * *